(12) United States Patent
Velculescu et al.

(10) Patent No.: US 12,331,361 B2
(45) Date of Patent: *Jun. 17, 2025

(54) METHODS AND SYSTEMS FOR IDENTIFICATION AND PRIORITIZATION OF MUTATION-DERIVED NEOANTIGENS

(71) Applicant: Personal Genome Diagnostics Inc., Baltimore, MD (US)

(72) Inventors: Victor Velculescu, Baltimore, MD (US); Theresa Zhang, Baltimore, MD (US); James Robert White, Baltimore, MD (US); Luis Diaz, Ellicott City, MD (US)

(73) Assignee: Personal Genome Diagnostics Inc., Baltimore, MD (US)

( * ) Notice: Subject to any disclaimer, the term of this patent is extended or adjusted under 35 U.S.C. 154(b) by 1571 days.

This patent is subject to a terminal disclaimer.

(21) Appl. No.: 16/731,724

(22) Filed: Dec. 31, 2019

(65) Prior Publication Data

US 2020/0160939 A1 May 21, 2020

Related U.S. Application Data

(63) Continuation of application No. 15/210,489, filed on Jul. 14, 2016, now Pat. No. 10,563,266.

(60) Provisional application No. 62/192,373, filed on Jul. 14, 2015.

(51) Int. Cl.

| | | |
|---|---|---|
| *C12Q 1/6886* | (2018.01) | |
| *C12N 15/10* | (2006.01) | |
| *G01N 33/574* | (2006.01) | |
| *G01N 33/68* | (2006.01) | |
| *G16B 20/00* | (2019.01) | |
| *G16B 20/20* | (2019.01) | |
| *G16B 20/30* | (2019.01) | |
| *G16B 20/40* | (2019.01) | |
| *G16B 35/00* | (2019.01) | |
| *G16B 35/20* | (2019.01) | |
| *G16C 20/20* | (2019.01) | |
| *G16C 20/50* | (2019.01) | |
| *G16C 20/60* | (2019.01) | |
| *G16C 20/70* | (2019.01) | |
| *G16H 10/40* | (2018.01) | |

(52) U.S. Cl.
CPC ....... *C12Q 1/6886* (2013.01); *C12N 15/1068* (2013.01); *C12N 15/1089* (2013.01); *G01N 33/574* (2013.01); *G01N 33/57484* (2013.01); *G01N 33/6878* (2013.01); *G16B 20/00* (2019.02); *G16B 20/20* (2019.02); *G16B 20/30* (2019.02); *G16B 20/40* (2019.02); *G16B 35/00* (2019.02); *G16B 35/20* (2019.02); *G16C 20/20* (2019.02); *G16C 20/50* (2019.02); *G16C 20/60* (2019.02); *G16C 20/70* (2019.02); *G16H 10/40* (2018.01); *C12Q 2600/136* (2013.01); *C12Q 2600/156* (2013.01); *G01N 2333/70539* (2013.01)

(58) Field of Classification Search
None
See application file for complete search history.

(56) References Cited

U.S. PATENT DOCUMENTS

2011/0293637 A1   12/2011   Hacohen et al.

FOREIGN PATENT DOCUMENTS

| WO | 2007/101227 A2 | 9/2007 |
|---|---|---|
| WO | WO 2007/101227 | 9/2007 |
| WO | 2014/052707 A2 | 4/2014 |

OTHER PUBLICATIONS

Larsen, M.V., Lundegaard, C., Lamberth, K. et al. Large-scale validation of methods for cytotoxic T-lymphocyte epitope prediction. BMC Bioinformatics vol. 8, 424 (Oct. 31, 2007).
Japanese Office Action issued Jul. 21, 2020, regarding JP 2018-501936.
Anonymous: Identify and Prioritize Candidate Neoantigens From Cancer Exome Sequencing Results With Unmatched Accuracy; PGD/Immunoselect, 2015. 1-2.
Fritsch et al., "HLA-Binding Properties of Tumor Neoepitopes in humans" Cancer Immunology Research, vol. 2, No. 6, pp. 522-529, 2014 (9 Pages).
International Preliminary Report on Patentability received for PCT Patent Application No. PCT/US2016/042288, mailed on Jan. 25, 2018, 8 pages.
International Search Report and Written Opinion of the International Searching Authority Mailed Oct. 20, 2016 for International Application No. PCT/US2016/042288 (12 Pages).
Ito et al., "Cancer Neoantigens: A Promising Source of Immunogens for Cancer Immunotherapy", Journal of Clinical & Cellular Immunology, vol. 6, Article No. 2, pp. 1-7, Apr. 2015 (7 Pages).

(Continued)

*Primary Examiner* — G. Steven Vanni
(74) *Attorney, Agent, or Firm* — Kilpatrick Townsend & Stockton LLP

(57) ABSTRACT

Cancer immunology provides promising new avenues for cancer treatment but validation of potential neoantigens to target is costly and expensive. Analysis of MHC binding affinity, antigen processing, similarity to known antigens, predicted expression levels (as mRNA or proteins), self-similarity, and mutant allele frequency, provides screening method to identify and prioritize candidate neoantigens using sequencing data. Methods of the invention thereby save time and money by identifying the priority candidate neoantigens for further experimental validation.

21 Claims, 4 Drawing Sheets
Specification includes a Sequence Listing.

(56) References Cited

OTHER PUBLICATIONS

Rajasagi et al., "Systematic Identification of Personal Tumor-Specific Neoantigens in Chronic Lymphocytic Leukemia", Blood, vol. 124, No. 3, pp. 453-462, 2014 (11 Pages).
Supplementary European Search Report and Search Opinion received for EP Patent Application No. 16825179.1, mailed on Feb. 12, 2019, 8 pages.
Szolek et al., "OptiType: Precision HLA Typing from Next-Generation Sequencing Data", Bioinformatics, vol. 30, No. 23, pp. 3310-3316, 2014 (7 Pages).
Van Buuren, M. M., Calis, J. J., & Schumacher, T. N. High sensitivity of cancer exome-based CD8 T cell neo-antigen identification. Oncoimmunology, 3(5), e28836. 2014.
Yadav, Mahesh et al.: "Predicting immunogenic tumour mutations by combining mass spectrometry and exome sequencing", Nov. 27, 2014. Nature, 515, 572-576.
CN Office Action in Chinese Application No. 201680050906.1, dated Dec. 1, 2019, 16 pages (with English translation).
Van Buuren et al., "High sensitivity of cancer exome-based CD8 T cell neo-antigen identification", OncoImmunology, May 2014, 3(5):e28836-1-e28836-6.
CA Application No. 2,992,578 , "Office Action", mailed on Oct. 16, 2023, 3 pages.
EP Application No. 16825179.1 , "Intention to Grant", mailed on Dec. 1, 2023, 8 pages.
"Identify and Prioritize Candidate Neoantigens from Cancer Exome Sequencing Results with Unmatched Accuracy," GD/Immunoselect, 2015, pp. 1-2.
Van Buuren, M. et al., "High Sensitivity of Cancer Exome-based CD8 T Cell Neo-Antigen Identification," Oncoimmunology, 3(5):e28836-1-e28836-6 (2014).
Yadav, M. et al., "Predicting Immunogenic Tumour Mutations by Combining Mass Spectrometry and Exome Sequencing," Nature, 515:572-576 (2014).
CA 2,992,578, Office Action, Oct. 3, 2022, 4 pages.
EP 16825179.1, Office Action, Oct. 20, 2022, 4 pages.

| Patient ID | HLA Type | Gene Name | Peptide ID | MUT Peptide | MUT HLA Affinity | MUT CTL Class | Mean Exp in Tumor | Priority |
|---|---|---|---|---|---|---|---|---|
| Patient 1 | HLA-A*02:01 | GAS7 | 1_p09490_10 | SLADEAEVYL | 14.4 | III | 236 | High |
| Patient 1 | HLA-B*44:03 | C9INF43 | 59_p0890XL8 | GLF0OYL | 5.72 | III | 4653 | High |
| Patient 1 | HLA-A*24:02 | PLA-O31 | 124_p11981_11 | KLLXXLNGWYM | 23.3 | III | 2063 | High |
| Patient 1 | HLA-A*02:01 | PRP18 | 197_p19240_11 | RLRKPLFFPRA | 16.63 | III | 111 | High |

FIG. 4

SEQUENCE LISTING

```
<160> NUMBER OF SEQ ID NOS: 23

<210> SEQ ID NO 1
<211> LENGTH: 10
<212> TYPE: PRT
<213> ORGANISM: Homo sapiens

<400> SEQUENCE: 1

Gly Ile Val Glu Gly Leu Ile Thr Thr Val
1               5                   10

<210> SEQ ID NO 2
<211> LENGTH: 9
<212> TYPE: PRT
<213> ORGANISM: Homo sapiens

<400> SEQUENCE: 2

Lys Glu Leu Glu Gly Ile Leu Leu Leu
1               5

<210> SEQ ID NO 3
<211> LENGTH: 9
<212> TYPE: PRT
<213> ORGANISM: Homo sapiens

<400> SEQUENCE: 3

Ser Tyr Leu Asp Ser Gly Ile His Phe
1               5

<210> SEQ ID NO 4
<211> LENGTH: 10
<212> TYPE: PRT
<213> ORGANISM: Homo sapiens

<400> SEQUENCE: 4

Leu Leu Leu Asp Asp Leu Leu Val Ser Ile
1               5                   10

<210> SEQ ID NO 5
<211> LENGTH: 10
<212> TYPE: PRT
<213> ORGANISM: Homo sapiens
```

```
<400> SEQUENCE: 5

Gly Leu Phe Gly Asp Ile Tyr Leu Ala Ile
1               5                   10

<210> SEQ ID NO 6
<211> LENGTH: 10
<212> TYPE: PRT
<213> ORGANISM: Homo sapiens

<400> SEQUENCE: 6

Leu Thr Asp Asp Arg Leu Phe Thr Cys Tyr
1               5                   10

<210> SEQ ID NO 7
<211> LENGTH: 9
<212> TYPE: PRT
<213> ORGANISM: Homo sapiens

<400> SEQUENCE: 7

Val Val Met Ser Trp Ala Pro Pro Val
1               5

<210> SEQ ID NO 8
<211> LENGTH: 9
<212> TYPE: PRT
<213> ORGANISM: Homo sapiens

<400> SEQUENCE: 8

Glu Ala Phe Ile Gln Pro Ile Thr Arg
1               5

<210> SEQ ID NO 9
<211> LENGTH: 9
<212> TYPE: PRT
<213> ORGANISM: Homo sapiens

<400> SEQUENCE: 9

Lys Ile Phe Ser Glu Val Thr Leu Lys
1               5

<210> SEQ ID NO 10
<211> LENGTH: 9
<212> TYPE: PRT
<213> ORGANISM: Homo sapiens

<400> SEQUENCE: 10

Cys Ile Leu Gly Lys Leu Phe Thr Lys
1               5

<210> SEQ ID NO 11
<211> LENGTH: 10
<212> TYPE: PRT
<213> ORGANISM: Homo sapiens

<400> SEQUENCE: 11

Ser Leu Ala Asp Glu Ala Glu Val Tyr Leu
1               5                   10

<210> SEQ ID NO 12
<211> LENGTH: 9
<212> TYPE: PRT
<213> ORGANISM: Homo sapiens

<400> SEQUENCE: 12
```

```
Ile Leu Asp Lys Val Leu Val His Leu
1               5

<210> SEQ ID NO 13
<211> LENGTH: 9
<212> TYPE: PRT
<213> ORGANISM: Homo sapiens

<400> SEQUENCE: 13

Tyr Thr Asp Phe His Cys Gln Tyr Val
1               5

<210> SEQ ID NO 14
<211> LENGTH: 9
<212> TYPE: PRT
<213> ORGANISM: Homo sapiens

<400> SEQUENCE: 14

Lys Thr Leu Thr Ser Val Phe Gln Lys
1               5

<210> SEQ ID NO 15
<211> LENGTH: 9
<212> TYPE: PRT
<213> ORGANISM: Homo sapiens

<400> SEQUENCE: 15

Lys Leu Tyr Glu Glu Pro Leu Leu Lys
1               5

<210> SEQ ID NO 16
<211> LENGTH: 9
<212> TYPE: PRT
<213> ORGANISM: Homo sapiens

<400> SEQUENCE: 16

Ile Leu Asn Ala Met Ile Ala Lys Ile
1               5

<210> SEQ ID NO 17
<211> LENGTH: 10
<212> TYPE: PRT
<213> ORGANISM: Homo sapiens

<400> SEQUENCE: 17

Lys Glu Phe Glu Asp Ile Ile Asn Trp
1               5                   10

<210> SEQ ID NO 18
<211> LENGTH: 9
<212> TYPE: PRT
<213> ORGANISM: Homo sapiens

<400> SEQUENCE: 18

Asp Tyr Leu Gln Tyr Val Leu Gln Ile
1               5

<210> SEQ ID NO 19
<211> LENGTH: 9
<212> TYPE: PRT
<213> ORGANISM: Homo sapiens

<400> SEQUENCE: 19

Gln Thr Ala Cys Glu Val Leu Asp Tyr
1               5
```

```
<210> SEQ ID NO 20
<211> LENGTH: 10
<212> TYPE: PRT
<213> ORGANISM: Homo sapiens

<400> SEQUENCE: 20

Thr Leu Asp Trp Leu Leu Gln Thr Pro Lys
1               5                   10

<210> SEQ ID NO 21
<211> LENGTH: 8
<212> TYPE: PRT
<213> ORGANISM: Homo sapiens

<400> SEQUENCE: 21

Gly Leu Phe Gly Asp Ile Tyr Leu
1               5

<210> SEQ ID NO 22
<211> LENGTH: 11
<212> TYPE: PRT
<213> ORGANISM: Homo sapiens

<400> SEQUENCE: 22

Lys Leu Leu Gln Gln Leu Asn Gly Trp Tyr Met
1               5                   10

<210> SEQ ID NO 23
<211> LENGTH: 11
<212> TYPE: PRT
<213> ORGANISM: Homo sapiens

<400> SEQUENCE: 23

Phe Leu Pro Lys Pro Leu Phe Phe Phe Arg Ala
1               5                   10
```

METHODS AND SYSTEMS FOR IDENTIFICATION AND PRIORITIZATION OF MUTATION-DERIVED NEOANTIGENS

CROSS-REFERENCE TO RELATED APPLICATIONS

This application is a continuation application of U.S. application Ser. No. 15/210,489 filed Jul. 14, 2016, now pending; which claims the benefit under 35 USC § 119(e) to U.S. Application Ser. No. 62/192,373 filed Jul. 14, 2015. The disclosure of each of the prior applications is considered part of and is incorporated by reference in the disclosure of this application.

INCORPORATION OF SEQUENCE LISTING

The material in the accompanying sequence listing is hereby incorporated by reference into this application. The accompanying sequence listing text file, named PGDX3040-2_ST25.txt, was created on Dec. 30, 2019 and is 4 kb in size. The file can be accessed using Microsoft Word on a computer that uses Windows OS.

BACKGROUND OF THE INVENTION

Field of the Invention

This invention is related to the area of neoantigen analysis. In particular, it relates to identification and prioritization of mutation-derived neoantigens for development of cancer vaccine and T-cell therapy.

Background Information

Cancer is characterized by proliferation of abnormal cells. The success of conventional treatments depends on the type of cancer and the stage at which it is detected. Many treatments include costly and painful surgeries and chemotherapies and are often unsuccessful or only modestly prolong a patient's life. Promising treatment methods in development include tumor vaccines or T-cell therapy that target tumor antigens enabling a patient's immune system to differentiate between tumor and healthy cells and to elicit an immune response in the patient. See Chen, et al., Oncology Meets Immunology: The Cancer-Immunity Cycle, Immunity 39, Jul. 25, 2013, the contents of which are incorporated herein for all purposes in their entirety.

Neoantigens are a class of immunogens associated with tumor-specific mutations unique to a patient's cancer. Neoantigens have shown promise as targets for antitumor immunity techniques including adaptive T-cell transfer with tumor infiltrating lymphocytes (TIL), cancer vaccines, and checkpoint inhibitors. See Hacohen, et al., Getting Personal with Neoantigen-Based Therapeutic Cancer Vaccines, Cancer Immunol Res, July 2013 1, 11; Robbins, et al., Mining exomic sequencing data to identify mutated antigens recognized by adoptively transferred tumor-reactive T cells, Nature Medicine 19, 747-752 (2013); the contents of each of which are incorporated herein for all purposes in their entirety.

While strategies exist for identifying and prioritizing candidate neoantigens using sequenced tumor DNA and HLA typing, conventional techniques lack sensitivity and specificity, failing to identify some candidate neoantigens and providing unfocussed results that still require expensive validation procedures. Snyder, et al., Genetic Basis for Clinical Response to CTLA-4 Blockade in Melanoma, N Engl J Med 2014; 371:2189-2199; Segal, et al., Epitope landscape in breast and colorectal cancer, Cancer Res. 2008 Feb. 1; 68(3):889-92; Fritsch, et al., 2014, HLA-Binding Properties of Tumor Neoepitopes in Humans, Cancer Immunol Res; 2(6); 1-8; the contents of each of which are incorporated herein for all purposes in their entirety.

SUMMARY OF THE INVENTION

The invention relates to screening methods for identifying and prioritizing candidate neoantigens. The invention recognizes key factors that operate together to prioritize neoantigens for effective treatment. As a result of this recognition, the invention provides a multivariate operation, using both genomic and protein-based information, to prioritize neoantigens for highly-personalized efficacy in cancer immunotherapy. Based upon application of the claimed methods, neoantigen priority is used to rank the peptide sequences as candidate neoantigens based upon the potential for clinical efficacy in the patient from whom a sample was taken.

In certain embodiments, methods of the invention utilize sequencing and matched normal controls to achieve high levels of sensitivity and positive predictive value in identifying mutations or variants, even at low mutant allele frequencies in the tumor. Once mutated sequences are identified in the tumor tissue, along with corresponding candidate neoantigen peptide sequences, a neoantigen priority score for each candidate neoantigen peptide sequence is produced using an individual's HLA type and two or more of the following: the peptide sequence's similarity to known antigens; the peptide sequence's self-similarity; mutant allele frequency for the peptide sequence; predicted major histocompatibility complex (MHC) binding affinity between the peptide sequence and one or more of the individual's HLA allele's, predicted antigen processing for the peptide sequence, and mRNA or protein expression analysis for the peptide sequence. Predicted antigen processing may include peptide cleavage prediction or a transporter associated with antigen processing (TAP) affinity prediction. The various inputs used to calculate neoantigen priority may be weighted in some embodiments. The priority score is used to identify and prioritize candidate neoantigens with a high probability of clinical utility based on sequencing data thereby focusing further investigations on only the most promising potential antigens. Accordingly, methods of the invention provide a screen that can save both time and money on costly experimental validation of neoantigens by providing a priority report to investigators to help increase their likelihood identifying a successful neoantigen with less additional experimentation.

In certain aspects, the invention provides methods for predicting and prioritizing potential neoantigens. Exemplary methods include obtaining a tumor nucleic acid sequence and a normal nucleic acid sequence for an individual. The tumor nucleic acid sequence is compared to the normal nucleic acid sequence to determine a plurality of possible translated peptide sequences having tumor-specific mutations. Then, an HLA type is determined for the individual where the HLA type includes one or more HLA alleles. Methods also include predicting a major histocompatibility complex (MHC) binding affinity between each of the plurality of peptide sequences and the HLA alleles and predicting an antigen peptide processing score for each of the plurality of peptide sequences. A mutant allele frequency is determined for each of the plurality of peptide sequences and each of the plurality of peptide sequences is compared to a known antigen to determine a known antigen similarity score. Methods of the invention further comprise determining a self-similarity score for each of the plurality of peptide sequences from the normal nucleic acid sequence and determining an mRNA expression level or a protein expression level for each of the plurality of peptide sequences. For each of the plurality of peptide sequences, a multivariate operation is performed using terms comprising the MHC binding affinity, the antigen peptide processing score, the known antigen similarity score, the self-similarity score, and the mRNA expression level or protein expression level, to produce a neoantigen priority score for each of the plurality of peptide sequences. A report is then prepared comprising the neoantigen priority score for each of the plurality of peptide sequences.

In certain embodiments, methods of the invention may include determining the tumor nucleic acid sequence through whole exome sequencing of a tumor nucleic acid extracted from a tumor tissue of the individual. The whole exome sequencing may include next generation sequencing or Sanger sequencing or both. In some embodiments, the normal reference nucleic acid sequence is obtained from a database of consensus sequence. In alternative embodiments, the normal nucleic acid sequence may be from a non-tumor tissue of the same individual from whom the sample is taken. Methods of the invention may include determining the normal nucleic acid sequence through whole exome sequencing of a normal nucleic acid obtained from the non-tumor tissue of the individual.

In various embodiments, the antigen peptide processing score may include a peptide cleavage prediction or a transporter associated with antigen processing (TAP) affinity prediction. The HLA type may be determined from the tumor nucleic acid sequence or the normal nucleic acid sequence or may be determined through serotyping, or by cellular assay. In certain embodiments, one or more steps of the method may be performed using a computer comprising a processor coupled to a tangible, non-transient memory and an input/output device. Methods of the invention may further include sending the report to the output device. In various methods of the invention, each of the plurality of peptide sequences may have a predicted MHC binding affinity, in IC50, of less than 500 nM. In certain embodiments, the known antigen sequence can be obtained from a database of known antigen sequences.

BRIEF DESCRIPTION OF THE DRAWINGS

FIG. 4 shows a sample report of the invention. Peptide sequences shown are as follows: SLADEAEVYL (SEQ ID NO: 11); GLFGDIYL (SEQ ID NO: 21); KLLQQLNGWYM (SEQ ID NO: 22); FLPKPLFFFRA (SEQ ID NO: 23).

DETAILED DESCRIPTION OF THE INVENTION

The invention provides methods for identifying and prioritizing candidate neoantigens for immunotherapeutic treatment of cancer. Methods of the invention utilize a multivariate analysis in order to provide a priority score for determining which candidate neoantigens are the most likely to be successful for development as a cancer immunotherapeutic. Methods of the invention are especially useful for determining individualized neoantigen priority in order to maximize treatment efficacy for a specific tumor in a specific patient. As a result of methods of the invention, clinicians are likely to have a better idea of which neoantigen treatment modalities to bring to clinical trials or to advance in clinical trials in order to produce an effective immunomodulatory therapeutic.

Data taken from tumor nucleic acid along with HLA typing, peptide similarity analysis and other indicia as described herein produce a score reflective of the potential therapeutic efficacy candidate neoantigens. Key inputs in the claimed multivariate analysis are provided herein. Those inputs combine to prioritize candidate neoantigens for further development. In certain embodiments, methods of the invention rely on whole exome sequencing and matched normal controls to achieve high levels of sensitivity and positive predictive value in identifying mutations or variants, even at low mutant allele frequencies. Once mutated sequences are identified along with corresponding candidate neoantigen peptide sequences for an individual, the weighted multivariate operation produces a neoantigen priority score for each candidate neoantigen peptide sequence using an individual's HLA type and two or more of the following: the peptide sequence's similarity to known antigens; the peptide sequence's self-similarity; mutant allele frequency for the peptide sequence; predicted major histocompatibility complex (MHC) binding affinity between the peptide sequence and one or more of the individual's HLA allele's, predicted antigen processing for the peptide sequence, and mRNA or protein expression analysis for the peptide sequence. Predicted antigen processing may include peptide cleavage prediction or a transporter associated with antigen processing (TAP) affinity prediction. Accordingly, methods of the invention provide a preliminary screen that can save both time and money on costly experimental validation of neoantigens by providing a priority report to investigators to help increase their likelihood identifying a successful neoantigen with less additional experimentation. Candidate neoantigens, as used herein may be given as peptides sequences.

Figure 1:
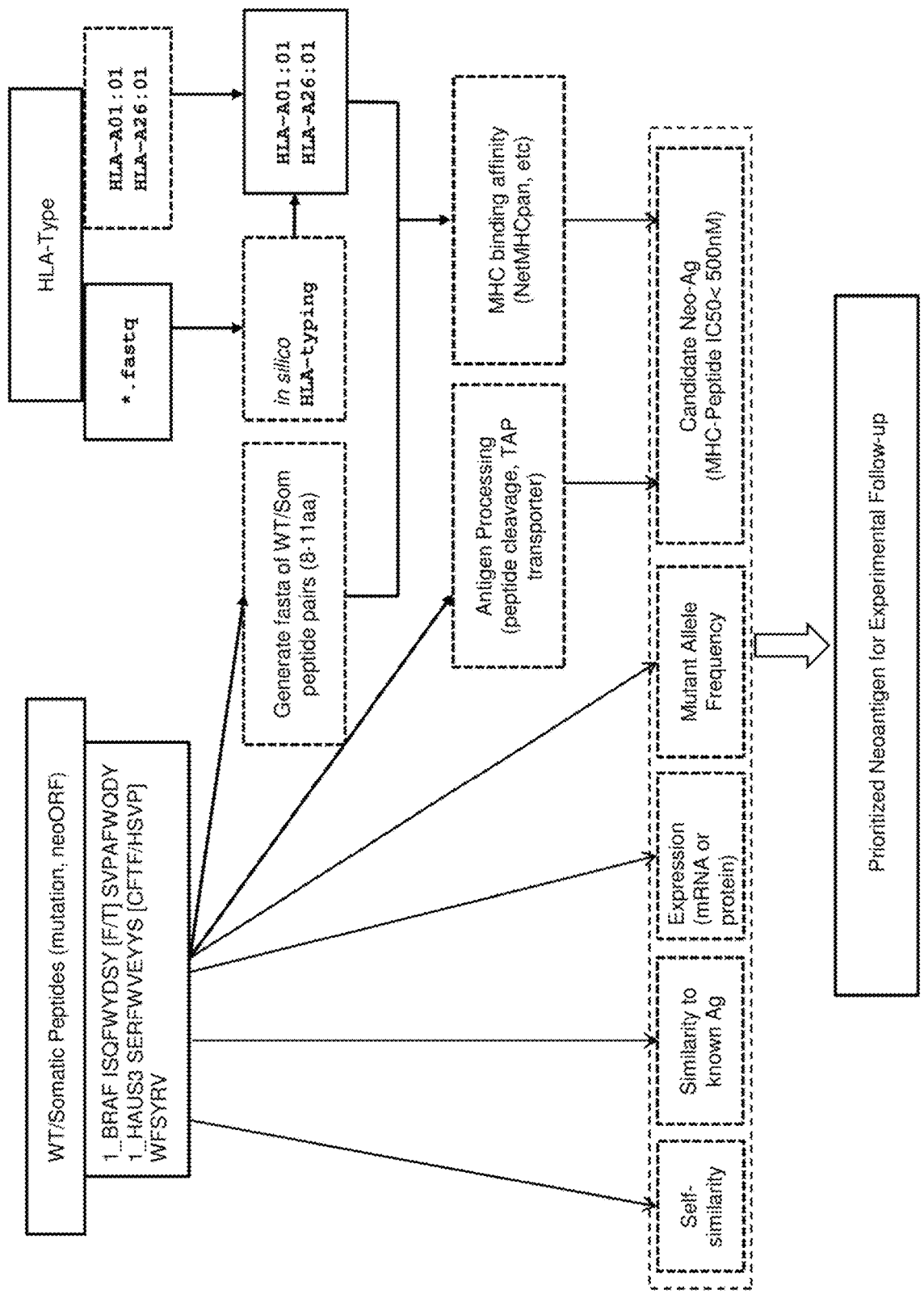
FIG. 1 diagrams a method for identifying and prioritizing candidate neoantigens.
Figure 2:
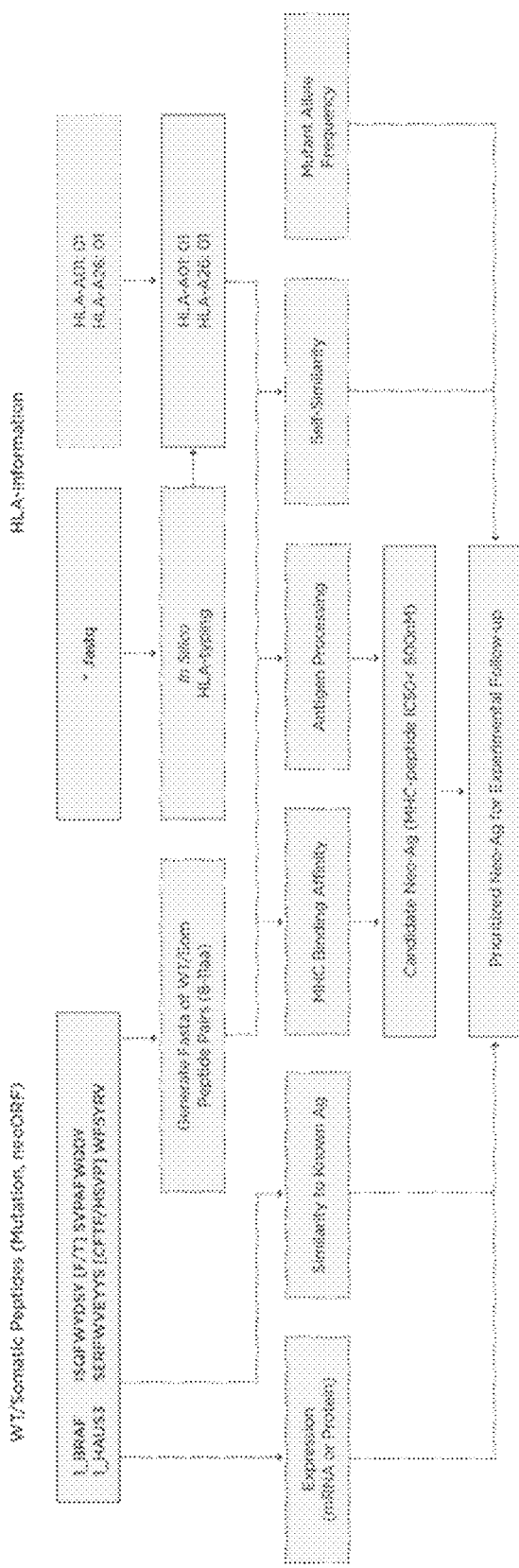
FIG. 2 diagrams another method for identifying and then prioritizing candidate neoantigens.

FIGS. 1 and 2 show exemplary methods of the invention comprising obtaining tumor nucleic acid sequencing data for an individual's tumor and normal nucleic acid sequencing data. Mutations are identified along with FASTA format data of wild type and somatic peptide pairs, typically between 8-11 amino acids in length. In various embodiments, wild type and somatic peptide pairs may be between 11 and 20 amino acids in length. FASTQ format nucleic acid sequencing data is used for in silico HLA-typing or alternatively, traditional experimentally validated HLA-typing information can be manually provided to the method (e.g., HLA-A01:01 HLA-A26:01).

Determined HLA alleles for the individual are used along with the FASTA format data of wild type and somatic peptide pairs to predict MHC binding affinity for the peptides and each HLA allele using, for example, NetMHCpan. The tumor nucleic acid sequencing data is used to predict antigen processing such as peptide cleavage and TAP transporter affinity. Antigen processing and MHC binding affinity predictions are then used to select candidate neoantigens or peptide sequences where, for example, predicted MHC binding affinity (in IC50) is less than 500 nM. The tumor nucleic acid sequence and the normal nucleic acid sequence are then used to assess self-similarity. Candidate neoantigens are also compared to known antigens to determine similarities and mRNA or protein expression is obtained for the genes harboring the peptides. The mutant allele frequency, expression, similarity to known antigens, self-similarity and predicted MHC binding affinity are then used in a weighted, multivariate operation, to produce a neoantigen priority score for each candidate neoantigen. This score can be used to prioritize neoantigens for experimental follow-up.

Sample Preparation, Sequencing and Mutation Identification

Methods of the invention may include identifying and prioritizing candidate neoantigens or peptide sequences from provided nucleic acid sequences or, in certain embodiments, may include sample preparation and sequencing techniques to generate nucleic acid sequences. In certain embodiments, samples from an individual or patient may be obtained in forms such as, Frozen tissue, FFPE blocks or slides, pleural effusion, cells, DNA, cell lines, blood, saliva, or xenografts. Samples may be obtained from a tumor tissue and, in certain embodiments, may also be obtained from a normal tissue to provide a source of normal or matched normal nucleic acid. Normal nucleic acid may be obtained from any non-tumor tissue or from sources such as saliva or whole blood. Tumor nucleic acids and normal nucleic acids may be extracted from the sample using known methods. In preferred embodiments, at least 50 ng of DNA should be obtained for sequencing.

Nucleic acids may comprise deoxyribonucleic acid (DNA) or ribonucleic acid (RNA). Nucleic acid samples may be sequenced using any known method. Nucleic acid samples may be sequenced using classic dideoxy sequencing reactions (Sanger method) using labeled terminators or primers and gel separation in slab or capillary. Other techniques which may be used with methods of the invention include sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, translocation through a nanopore or nanochannel, digestion or polymerization of DNA combined with detection of nucleotides in a nanopore or nanochannel, optical detection of nucleotides in strands localized with a nanopore or nanochannel, and SOLiD sequencing. Separated molecules may be sequenced by sequential or single extension reactions using polymerases or ligases as well as by single or sequential differential hybridizations with libraries of probes.

In some embodiments, a sequencing technique (e.g., a next-generation sequencing technique) is used to sequence part of one or more captured targets (e.g., or amplicons thereof) and the sequences are used to count the number of different barcodes that are present. Accordingly, in some embodiments, aspects of the invention relate to a highly-multiplexed qPCR reaction.

A sequencing technique that can be used includes, for example, Illumina sequencing. Illumina sequencing is based on the amplification of DNA on a solid surface using fold-back PCR and anchored primers. DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated. Sequencing according to this technology is described in U.S. Pat. Nos. 7,960,120; 7,835,871; 7,232,656; 7,598,035; 6,911,345; 6,833,246; 6,828,100; 6,306,597; 6,210,891; U.S. Pub. 2011/0009278; U.S. Pub. 2007/0114362; U.S. Pub. 2006/0292611; and U.S. Pub. 2006/0024681, each of which is incorporated by reference in their entirety.

Sequencing generates a plurality of reads. Reads generally include sequences of nucleotide data less than about 150 bases in length, or less than about 90 bases in length. In certain embodiments, reads are between about 80 and about 90 bases, e.g., about 85 bases in length. In some embodiments, these are very short reads, i.e., less than about 50 or about 30 bases in length.

A sequencing technique that can be used in the methods of the provided invention includes, for example, 454 sequencing (454 Life Sciences, a Roche company, Branford, Conn.) (Margulies, M et al., Nature, 437:376-380 (2005); U.S. Pat. Nos. 5,583,024; 5,674,713; and 5,700,673). 454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used in the methods of the provided invention is SOLiD technology by Applied Biosystems from Life Technologies Corporation (Carlsbad, Calif.). In SOLiD sequencing, DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

Another example of a DNA sequencing technique that can be used in the methods of the provided invention is Ion Torrent sequencing, described, for example, in U.S. Pubs. 2009/0026082, 2009/0127589, 2010/0035252, 2010/0137143, 2010/0188073, 2010/0197507, 2010/0282617, 2010/0300559, 2010/0300895, 2010/0301398, and 2010/0304982, the content of each of which is incorporated by reference herein in its entirety. In Ion Torrent sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and are attached at a resolution such that the fragments are individually resolvable. Addition of one or more nucleotides releases a proton (H.sup.+), which signal is detected and recorded in a sequencing instrument. The signal strength is proportional to the number of nucleotides incorporated.

Another example of a sequencing technology that can be used in the methods of the provided invention is Illumina sequencing. Illumina sequencing is based on the amplification of DNA on a solid surface using fold-back PCR and anchored primers. DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated. Sequencing according to this technology is described in U.S. Pub. 2011/0009278, U.S. Pub. 2007/0114362, U.S. Pub. 2006/0024681, U.S. Pub. 2006/0292611, U.S. Pat. Nos. 7,960,120, 7,835,871, 7,232,656, 7,598,035, 6,306,597, 6,210,891, 6,828,100, 6,833,246, and 6,911,345, each of which are herein incorporated by reference in their entirety.

Another example of a sequencing technology that can be used in the methods of the provided invention includes the single molecule, real-time (SMRT) technology of Pacific Biosciences (Menlo Park, Calif.). In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in and out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used in the methods of the provided invention is nanopore sequencing (Soni, G. V., and Meller, A., Clin Chem 53: 19962001 (2007)). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used in the methods of the provided invention involves using a chemical-sensitive field effect transistor (chemFET) array to sequence DNA (for example, as described in U.S. Pub. 2009/0026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used in the methods of the provided invention involves using an electron microscope (Moudrianakis E. N. and Beer M., PNAS, 53:564-71(1965)). In one example of the technique, individual DNA molecules are labeled using metallic labels that are distinguishable using an electron microscope. These molecules are then stretched on a flat surface and imaged using an electron microscope to measure sequences.

Another example of a sequencing technique that can be used in the methods of the provided invention involves Fast Aneuploidy Screening Test-Sequencing System (FAST-SeqS), as described in PCT application PCT/US2013/033451, which is incorporated by reference. See also Kinde et al., "FAST-SeqS: A Simple and Efficient Method for the Detection of Aneuploidy by Massively Parallel Sequencing," DOI: 10.1371/journal.pone.0041162, which is incorporated by reference. FAST-SeqS uses specific primers, specifically, a single pair of primers that anneal to a subset of sequences dispersed throughout the genome. The regions are selected due to similarity so that they could be amplified with a single pair of primers, but sufficiently unique to allow most of the amplified loci to be distinguished. FAST-SeqS yielded sequences align to a smaller number of positions, as opposed to traditional whole genome amplification libraries in which each tag must be independently aligned.

Sequence assembly can be accomplished by methods known in the art including reference-based assemblies, de novo assemblies, assembly by alignment, or combination methods. In some embodiments, sequence assembly uses the low coverage sequence assembly software (LOCAS) tool described by Klein, et al., in LOCAS-A low coverage sequence assembly tool for re-sequencing projects, PLoS One 6(8) article 23455 (2011), the contents of which are hereby incorporated by reference in their entirety. Sequence assembly is described in U.S. Pat. Nos. 8,165,821; 7,809,509; 6,223,128; U.S. Pub. 2011/0257889; and U.S. Pub. 2009/0318310, the contents of each of which are hereby incorporated by reference in their entirety.

Tumor nucleic acid sequences, once obtained, may be compared to a normal nucleic acid sequence to determine mutations in the tumor nucleic acid sequence. In certain embodiments, the normal nucleic acid may be a reference genome such as HG18 or HG19 or any human reference sequence compiled by the International Human Genome Sequencing Consortium or the 1000 genomes project. In preferred embodiments, the normal nucleic acid sequence is a matched normal nucleic acid which may be obtained from a non-tumor tissue of the individual or from a related individual. Using a matched normal tissue as a reference sequence for calling variants or mutations may help identify germline mutations present in both tumor and non-tumor cells of the individual and can allow elimination of false-positives and more accurate identification of tumor-specific variants or mutations. FIG. 2 shows a bar graph illustrating germline and somatic changes detected in a series of cases which shows the importance of using a matched normal to identify tumor-specific mutations. Mutations, as used herein, can include, for example, modifications, chromosomal alterations, substitutions, indels, single nucleotide polymorphisms, translocations, inversions, duplications, and copy number variations.

In an exemplary embodiment, tumor-specific mutations are identified using a commercially available technique such as CANCERXOME available from Personal Genome Diagnostics, Inc. (Baltimore, Maryland).

HLA Typing

HLA typing of the individual or patient may be conducted using a variety of known means including, cellular assay, serotyping, gene typing, or in silico from sequence data.

In a preferred embodiment, HLA typing is conducted in silico using one or more techniques such as OptiType, run on a computing device. See Szolek, et al., OptiType: precision HLA typing from next-generation sequencing data, Bioinformatics. 2014 Dec. 1; 30(23), incorporated herein in its entirety for all purposes. A variety of other in silico techniques may also be used. See Major, et al., HLA typing from 1000 genomes whole genome and whole exome illumina data, PLoS One. 2013 Nov. 6; 8(11):e78410; Wittig, et al., Development of a high-resolution NGS-based HLA-typing and analysis pipeline, Nucl. Acids Res. (2015) first published online Mar. 9, 2015 doi:10.1093/nar/gkv184.

In certain embodiments, HLA alleles may be determined by other means (e.g., HLA-A01:01, HLA-A26:01) and the results can also be utilized by the method, thereby avoiding the need for in silico prediction.

Identifying Candidate Neoantigens and Prioritizing Candidate Neoantigens

Using HLA typing information for the individual as well as peptide sequences with identified mutations, MHC binding affinity can be predicted for each peptide sequence using a variety of in silico techniques and computer programs such as a version of NetMHCpan available at the Technical University of Denmark (e.g., version 2.8), MHC-I Antigenic Peptide Processing Prediction (MAPPP) available at the Max-Planck-Institut für Infektionsbiologie, Berlin, the Bio-Informatics and Molecular Analysis Section (BIMAS) HLA Peptide Binding Predictions available at the National Institutes of Health (NIH), Rankpep MHC-peptide binding prediction available at the Universidad Complutense de Madrid, Immunomedicine Group, or the SYFPEITHI epitope predictor.

Prior to MHC presentation and binding, correct peptide processing must occur including peptide cleavage and transporter associated with antigen processing (TAP). According to methods of the invention, candidate neoantigens may be identified using, in part, antigen peptide processing prediction which may include an antigen peptide processing score. In certain embodiments, antigen peptide processing scores may comprise peptide cleavage prediction and TAP binding affinity prediction. Peptide cleavage may be predicted from a peptide sequence using an in silico technique or computer program such as the MAPPP proteasome cleavage predictor available at the Max-Planck-Institut für Infektionsbiologie, Berlin or the Rankpep Cleavage Predictor available at the Universidad Complutense de Madrid, Immunomedicine Group. Similarly, TAP binding affinity may be predicted from the peptide sequence using known methods such as described in Doytchinova, et al., Transporter associated with antigen processing preselection of peptides binding to the MHC: a bioinformatic evaluation, J Immunol. 2004 Dec. 1; 173(11); Tenzer, et al., Modeling the MHC class I pathway by combining predictions of proteasomal cleavage, TAP transport and MHC class I binding, Cell Mol Life Sci. 2005 May; 62(9):1025-37; Zhang, et al., PREDTAP: a system for prediction of peptide binding to the human transporter associated with antigen processing, Immunome Research May 2006, 2:3; the contents of which are incorporated by reference herein in their entirety and for all purposes.

Based on the antigen peptide processing prediction or score, candidate neoantigens may be given an antigen peptide processing classification of epitope (E) or non-antigen (NA) where an E classification is prioritized over an NA classification.

Using a MHC binding affinity cutoff such as, for example, an IC50 value of less than 100 nM, 200 nM, 300 nM, 400 nM, 500 nM, 600 nM, 700 nM, 800 nM, 900 nM, 1000 nM, etc., candidate neoantigens or peptide sequences with predicted MHC binding affinities above the cutoff may be eliminated from further analysis or consideration.

Candidate neoantigens may be further characterized through analysis of their similarity to known antigens, predicted expression levels (as mRNA or proteins), a self-similarity measure, and mutant allele frequency. Mutant allele frequency can be determined through analysis of tumor nucleic acid sequencing data to determine the frequency with which the subject mutant allele appears in sequenced nucleic acid compared to other alleles of that nucleic acid or gene. Mutant allele frequency may be determined as, for example, mean expression in tumor nucleic acid. Generally, increased mutant allele frequency will be indicative of an increased likelihood of clinical utility for a peptide sequence or candidate neoantigen.

Self-similarity may be determined by comparing the mutant peptide sequence to an equivalent normal peptide sequence in order to establish a similarity score. In certain embodiments, self-similarity may be determined amino acid by amino acid along a peptide sequence. Self-similarity may be determined as a percentage value. Generally, a lower level of self-similarity will be indicative of an increased likelihood of clinical utility for a peptide sequence or candidate neoantigen. In a preferred embodiment, the PMBEC matrix of amino acid substitutions is used to compute a similarity score, with scores less than 0.05 reflecting a loss of similarity to the parental wildtype peptide in the mutant peptide. (See Kim et al., Derivation of an amino acid similarity matrix for peptide:MHC binding and its application as a Bayesian prior, *BMC Bioinformatics* 2009 10:394).

Known antigen similarity may be determined by comparing the peptide sequence to peptide sequences of known antigens. In certain embodiments, known antigen similarity may be determined amino acid by amino acid along a peptide sequence. Known antigens may be obtained from a database such as the Immune Epitope Database and Analysis Resource (iedb). A peptide sequence or candidate neoantigen may be given a score which may comprise, for example, a percentage similarity value which may be the highest determined value from a series of comparisons to a variety of known antigens. Generally, a higher level of similarity to known antigens will be indicative of an increased likelihood of clinical utility for a peptide sequence or candidate neoantigen. Known antigen similarity may be determined, for example, by a sequence similarity search of neoantigen candidates against the IEDB looking for sequence homology to known antigens or through a search against other databases of bacterial proteins which may reflect novel antigens.

Protein or mRNA expression levels may be predicted for a peptide sequence by, for example measuring the expression of the associated gene in a tumor sample using RNAseq analysis or microarrays or by referring to a database of known expression data associated with specific tumor types (e.g., The Cancer Genome Atlas).

In various embodiments a multivariate operation may be performed on terms representing two or more of the following MHC binding affinity, antigen peptide processing score, known antigen similarity score, self-similarity score, and mRNA expression level or protein expression level, to produce a neoantigen priority score for each of the plurality of peptide sequences. In various embodiments one or more of the terms may be weighted using a weight value to increase or decrease its impact on the neoantigen priority score relative to the other terms.

In an exemplary embodiment, neoantigen priority may be determined through application of a rule or series of rules to one or more characteristics determined or identified for each of a plurality of candidate neoantigens. Rules may comprise exclusionary provisions and multi-factor sorting parameters that prioritize neoantigen candidate characteristics such as MHC binding affinity, antigen peptide processing score or classification, known antigen similarity, self-similarity score, and mRNA expression level or protein expression level. Examples of such embodiments may be found below.

Figure 3:
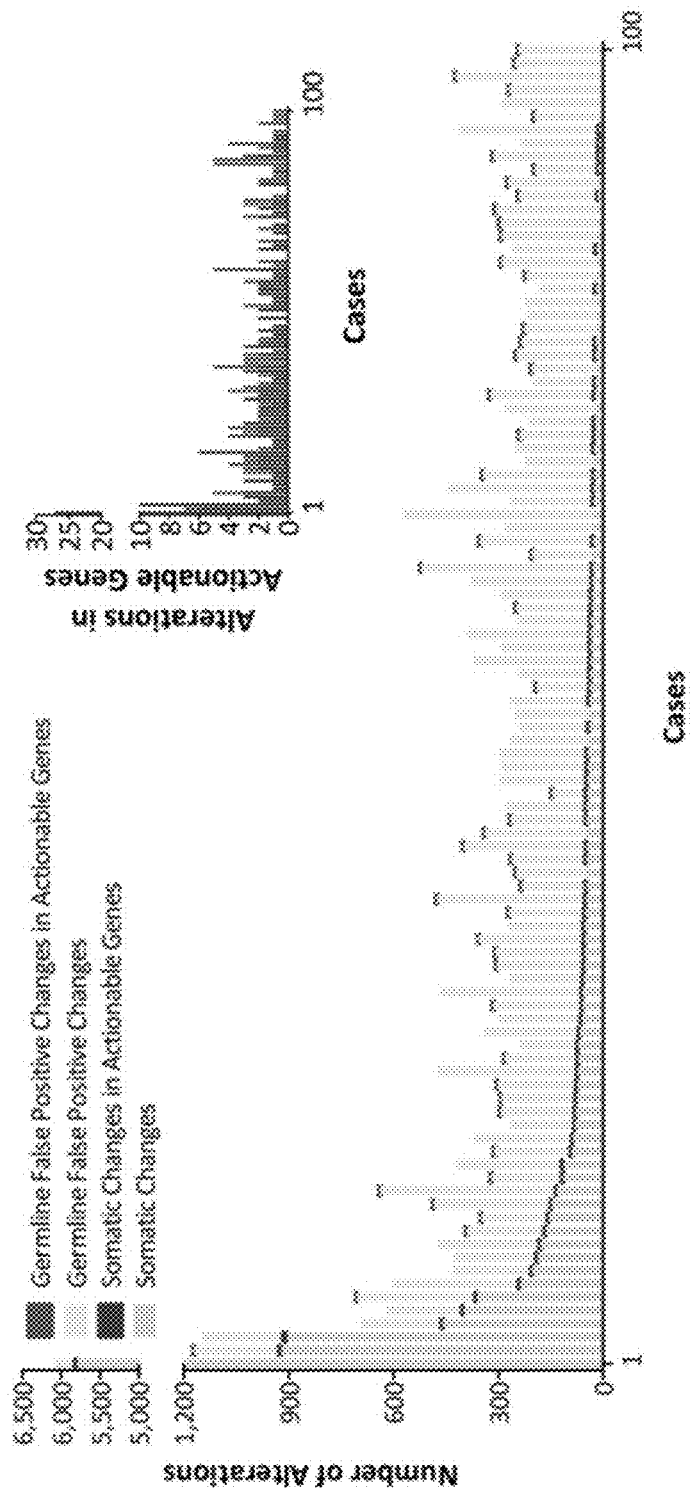
FIG. 3 shows a graph illustrating germline and somatic changes detected in a series of cases and the importance of using a matched normal to identify tumor-specific mutations.

In certain embodiments, the neoantigen prioritization ranking may be included in a report prepared according to methods of the invention. A sample report is shown in FIG. 3. The report may consist of any combination of a number of identified candidate neoantigens or peptide sequences, the associated neoantigen priority score, values for any combination of the determinative terms. In certain embodiments the candidate neoantigens may be ordered by, for example priority from highest to lowest. Reports may be physical in nature, printed or written on paper using an output device as described below or may be electronic, prepared and stored on a computing device. Reports may be sent to interested parties such as the tested individual or patient, an ordering or other physician or laboratory, or other entities. Reports may be delivered in a physical form or may be sent electronically by, for example, electronic mail.

Computing Devices

As one skilled in the art recognizes as necessary or best-suited for performance of the methods of the invention may include one or more computing devices, computing systems, or computers that include one or more of a processor (e.g., a central processing unit (CPU), a graphics processing unit (GPU), etc.), a computer-readable storage device (e.g., main memory, static memory, etc.), or combinations thereof which communicate with each other via a bus.

A processor may include any suitable processor known in the art, such as the processor sold under the trademark XEON E7 by Intel (Santa Clara, CA) or the processor sold under the trademark OPTERON 6200 by AMD (Sunnyvale, CA).

Memory preferably includes at least one tangible, non-transitory medium capable of storing: one or more sets of instructions executable to cause the system to perform functions described herein (e.g., software embodying any methodology or function found herein or computer programs referred to above); data (e.g., images of sources of medication data, personal data, or a database of medications); or both. While the computer-readable storage device can, in an exemplary embodiment, be a single medium, the term "computer-readable storage device" should be taken to include a single medium or multiple media (e.g., a centralized or distributed database, and/or associated caches and servers) that store the instructions or data. The term "computer-readable storage device" shall accordingly be taken to include, without limit, solid-state memories (e.g., subscriber identity module (SIM) card, secure digital card (SD card), micro SD card, or solid-state drive (SSD)), optical and magnetic media, and any other tangible storage media.

Any suitable services can be used for storage such as, for example, Amazon Web Services, memory of the computing system, cloud storage, a server, or other computer-readable storage.

Input/output devices according to the invention may include one or more of a display unit (e.g., a liquid crystal display (LCD) or a cathode ray tube (CRT) monitor), an alphanumeric input device (e.g., a keyboard), a cursor control device (e.g., a mouse or trackpad), a disk drive unit, a printer, a signal generation device (e.g., a speaker), a touchscreen, a button, an accelerometer, a microphone, a cellular radio frequency antenna, a network interface device, which can be, for example, a network interface card (NIC), Wi-Fi card, or cellular modem, or any combination thereof.

One of skill in the art will recognize that any suitable development environment or programming language may be employed to implement the methods described herein. For example, methods herein can be implemented using Perl, Python, C++, C#, Java, JavaScript, Visual Basic, Ruby on Rails, Groovy and Grails, or any other suitable tool. For a mobile device, it may be preferred to use native xCode or Android Java.

EXAMPLES

Example 1

In an exemplary embodiment, given a set of candidate neoantigen peptides, which may be determined by their association with somatic mutations determined through sequence analysis, the following set of rules may be applied. MHC binding affinity may be determined as described above to determine predicted IC50 affinity. All candidate neoantigens with a predicted IC50 affinity greater than, for example, 500 nM may then be removed from further examination.

The remaining candidate neoantigens may then be sorted according to a multi-factor sort starting with MHC binding affinity classification. Candidate neoantigens may be classified as SB or WB (strong binder and weak binder) as described above and sorted so that SB peptides are given a higher priority over WB peptides.

Antigen peptide processing may then be determined or predicted for the candidate neoantigens as described above. Candidate neoantigens may then be classified as E or NA and sub-sorted within their MHC binding affinity classification rankings so that SB peptides classified as E are prioritized over SB peptides classified as NA, which in turn are prioritized over WB peptides classified as E.

Reference gene expression level can then be determined for the candidate neoantigens according to the methods described above. The candidate neoantigens may then be sub-sorted, within their existing MHC binding affinity and antigen processing priority, by reference gene expression level with higher levels having a higher priority than lower levels.

The resulting ordered list of candidate neoantigens may comprise the prioritized set of candidate neoantigens, with the highest priority candidates at the top of the list. This list may be presented in the form of a report as described elsewhere and delivered to a requesting individual or entity.

In certain embodiments, methods may include, after ranking candidate neoantigens, treating a patient with a vaccine or T-cell therapy targeting a neoantigen based on its ranking. Methods may include experimentally validating candidate neoantigens based on their rankings. Methods may also include causing the treatment of a patient with a vaccine or T-cell therapy targeting a neoantigen based on its ranking.

Example 2

In a second exemplary embodiment, given a set of candidate neoantigen peptides, which may be determined by their association with somatic mutations determined through sequence analysis, the following set of rules may be applied. MHC binding affinity may be determined as described above to determine predicted IC50 affinity. All candidate neoantigens with a predicted IC50 affinity greater than, for example, 1000 nM may then be removed from further examination.

RNAseq expression values may be determined for the remaining candidate neoantigens and peptides with associated gene RNAseq expression values below a threshold of about 10 reads per kilobase per million reads mapped (RPKM) may be removed from further examination.

The remaining candidate neoantigens may then be sorted according to a multi-factor sort starting with MHC binding affinity classification. Candidate neoantigens may be classified as SB or WB as described above and sorted so that SB peptides are given a higher priority over WB peptides.

Antigen peptide processing may then be determined or predicted for the candidate neoantigens as described above. Candidate neoantigens may then be classified as E or NA and sub-sorted within their MHC binding affinity classification rankings so that SB peptides classified as E are prioritized over SB peptides classified as NA, which in turn are prioritized over WB peptides classified as E.

Self-similarity for the candidate neoantigens may then be determined using PMBEC comparison as described above. The candidate neoantigens may then be sub-sorted, within their existing MHC binding affinity and antigen processing priority, by self-similarity score with lower scores having a higher priority than higher scores.

The resulting ordered list of candidate neoantigens may comprise the prioritized set of candidate neoantigens, with the highest priority candidates at the top of the list. This list may be presented in the form of a report as described elsewhere and delivered to a requesting individual or entity.

Example 3

In a third exemplary embodiment, given a set of candidate neoantigen peptides, which may be determined by their association with somatic mutations determined through sequence analysis, the following set of rules may be applied. MHC binding affinity may be determined as described above to determine predicted IC50 affinity. All candidate neoantigens with a predicted IC50 affinity greater than, for example, 750 nM may then be removed from further examination.

RNAseq expression values may be determined for the remaining candidate neoantigens and peptides with associated gene RNAseq expression values below a threshold of about 25 reads per kilobase per million reads mapped (RPKM) may be removed from further examination The remaining candidate neoantigens may then be sorted according to a multi-factor sort starting with MHC binding affinity classification. Candidate neoantigens may be classified as SB or WB as described above and sorted so that SB peptides are given a higher priority over WB peptides.

Antigen peptide processing may then be determined or predicted for the candidate neoantigens as described above. Candidate neoantigens may then be classified as E or NA and sub-sorted within their MHC binding affinity classification rankings so that SB peptides classified as E are prioritized over SB peptides classified as NA, which in turn are prioritized over WB peptides classified as E.

Similarity to known antigens may then be determined for the candidate neoantigen according to, for example, the methods described above. The candidate neoantigens may then be sub-sorted based on 100% identity amino acid matches to known antigens (with longer perfect matches reflecting higher priority).

The resulting ordered list of candidate neoantigens may comprise the prioritized set of candidate neoantigens, with the highest priority candidates at the top of the list. This list may be presented in the form of a report as described elsewhere and delivered to a requesting individual or entity. The list may be used to experimentally validate or select, administer, or cause to be administered a treatment comprising a vaccine or T-cell therapy targeting a prioritized candidate neoantigen from the list.

Example 4

Using sequencing data; known neoantigens from Fritsch et al., Cancer Immunol Res 2014; experimentally validated neoantigens from Robbins et al. Nat Med 2013; and predictive biomarkers for checkpoint inhibitors determined using the techniques from Snyder et al. NEJM 2014; methods of the invention were applied to sequencing data and the prioritized peptide sequences or candidate neoantigens were compared to the validated neoantigens using the application of the rule set described in example 1.

The number of prioritized candidate neoantigens produced by the operation and the rank of experimentally validated neoantigens from Robbins et al. Nat Med 2013 are shown in table 1 below:

TABLE 1

| Sample | #Mutations | #Neo-Ag (IC50 < 500 nM) | #Neo-Ag Post Prioritization | Rank of Validated Neo-Ag |
|---|---|---|---|---|
| Patient 1 | 504 | 128 | 55 | 1, 14, 15, 16 |
| Patient 2 | 257 | 277 | 30 | 1, 2, 3, 4, 15, 16 |
| Patient 3 | 58 | 97 | 30 | 9, 10, 14, 15, 16 |

The operation ranked experimentally validated neo-antigens within the top 20% of all candidate neoantigens.

Comparison of the operation identified candidate neoantigens to the known neoantigens from Fritsch et al., Cancer Immunol Res 2014 revealed that the operation identified 18 of 19 of the known neoantigens as shown in table 2 for a sensitivity greater than 90%.

TABLE 2

| HLA Type | Gene Name | Peptide ID | Peptide (SEQ ID NO) | MHC Binding Affinity | MHC Binding Affinity Classification | Mut CTL Class | Mean Exp in Tumors |
|---|---|---|---|---|---|---|---|
| HLA-A*02:01 | GAPDH | 1 p09470_10 | GIVEGLITTV (SEQ ID NO: 1) | 17.86 | SB | E | 82563.87 |
| HLA-B*44:03 | OS9 | 1 p16401_9 | KELEGILLL (SEQ ID NO: 2) | 273.72 | SB | E | 7650.05 |
| HLA-A*24:02 | CTNNB1 | 1 p06113_9 | SYLDSGIHF (SEQ ID NO: 3) | 81.7 | SB | E | 7200.02 |
| HLA-A*02:01 | PRDXS | 1 p17810_10 | LLLDDLLVSI (SEQ ID NO: 4) | 5.22 | SB | E | 5098.34 |
| HLA-A*02:01 | CSNK1A1 | 1 p06000_10 | GLFGDIYLAI (SEQ ID NO: 5) | 10.32 | SB | E | 4594.90 |
| HLA-A*01:01 | PLEKHM2 | 1 p17325_10 | LTDDRLFTCY (SEQ ID NO: 6) | 4.4 | SB | E | 1995.86 |
| HLA-A*02:01 | FNDC3B | 1 p09141_9 | VVMSWAPPV (SEQ ID NO: 7) | 3.83 | SB | E | 1853.78 |
| HLA-A*68:01 | DDX21 | 1 p06503_9 | EAFIQPITR (SEQ ID NO: 8) | 8.72 | SB | E | 1526.82 |
| HLA-A*03:01 | SIRT2 | 1 p19975_9 | KLFSEVTLK (SEQ ID NO: 9) | 11.68 | SB | E | 1319.08 |
| HLA-A*11:01 | CDK12 | 1 p04954_9 | CLGKLFTK (SEQ ID NO: 10) | 27.31 | SB | E | 1157.82 |
| HLA-A*02:01 | GAS7 | 1 p09490_10 | SLADEAEVYL (SEQ ID NO: 11) | 14.4 | SB | E | 1135.96 |
| HLA-A*02:01 | CLPP | 1 p05462_9 | iLDKVLVHL (SEQ ID NO: 12) | 24.98 | SB | E | 1064.40 |
| HLA-A*01:01 | PPP1R3B | 1 p17694_9 | YTDFHCQYV (SEQ ID NO: 13) | 151.23 | SB | E | 869.06 |
| HLA-A*11:01 | MATN2 | 1 p13970_9 | KTLTSVFQK (SEQ ID NO: 14) | 6.23 | SB | E | 775.23 |
| HLA-A*03:01 | ATR | 1 p02119_9 | KLYEEPLLK (SEQ ID NO: 15) | 12.55 | SB | E | 679.24 |

TABLE 2-continued

| HLA Type | Gene Name | Peptide ID | Peptide (SEQ ID NO) | MHC Binding Affinity | MHC Binding Affinity Classification | Mut CTL Class | Mean Exp in Tumors |
|---|---|---|---|---|---|---|---|
| HLA-A*02:01 | HAUS3 | 1 p10334_9 | LLNAMIAKI (SEQ ID NO: 16) | 45.62 | SB | E | 342.94 |
| HLA-B*44:03 | BCL2A1 | 1 p02695_10 | KEFEDDIINW (SEQ ID NO: 17) | 35.3 | SB | E | 220.82 |
| HLA-A*24:02 | BCL2A1 | 1 p02695_9 | DYLQYVLQI (SEQ ID NO: 18) | 82.21 | SB | E | 220.82 |
| HLA-A*01:01 | KIAA1440 | 1 p12289_9 | QTACEVLDY (SEQ ID NO: 19) | 72.79 | SB | E | No Data from TCGA |
| HLA-A*03:01 | GPNMB | 1 p09948_10 | TLDWLLQTPK (SEQ ID NO: 20) | 273.98 | WB | NA | 7247.13 |

Example 5

Using cancer genomic data sets (e.g., TCGA) and cancer mutation databases (e.g., COSMIC), we identified over 1000 recurrent mutations that occurred with at least 1% frequency in any tumor type. We then predicted protein regions flanking the mutations as well as neoORFs due to frame-shift mutations. The most prevalent HLA class I alleles for the North American population were compiled using dbMHC from NCBI, resulting in 90 unique 4-digit alleles, each with a population frequency ≥0.15%.

Methods of the invention were applied to over 1000 somatic-mutation-associated peptides and the 90 HLA alleles to predict and prioritize the candidate neoantigens. Table 3 provides a partial list of the recurrent somatic mutations where the mutation-associated peptides are predicted to be candidate neoantigens to at least one of the HLA alleles compiled. The reported frequencies of HLA alleles in the North American population allows for assessment of the probability that a patient with a specific neoantigen-associated somatic mutation will have at least one of the HLA alleles that recognizes that neoantigen.

The recurrent somatic mutations identified here may lead to neoantigens that are potentially promising targets for effective vaccines and T-cell therapies. Because those antigens are exclusively expressed on tumor cells and not on any other cells, vaccines and T-cell therapies targeting them will mount a focused and immune response with reduced cytotoxicity. Moreover, because those mutations occur in multiple patients, the majority of them may confer growth advantage for the tumors thus will impede tumor growth once eradicated. Furthermore, for many mutations the resulting candidate neoantigens may bind to HLA alleles in substantial subsets of the North American population, suggesting that the vaccine or T-cell therapies targeting such neoantigens may potentially benefit many patients. Not surprisingly, a number of the mutations identified by the analysis outlined above have already been demonstrated to induce antitumor immunity, including IDH 1-R132H (Schumacher et al., Nature 2014), KRAS-G12 mutations (Chaft et al., Clin Lung Cancer 2014) and EGFR-VIII deletion (Taylor et al., Curr Cancer Drug Targets 2012).

TABLE 3

| GeneID | AA Mut | #Candidate Neoantigens | #HLA Class I Alleles with Predicted Binding | % North American Population Affected | Max Prevalence of Mutation in TCGA Major Cancer Types |
|---|---|---|---|---|---|
| BRAF | p.V600E | 4 | 9 | 7% | 30% |
| KRAS | p.G12C | 7 | 11 | 48% | 16% |
| PIK3CA | p.H 1047R | 9 | 13 | 39% | 14% |
| KRAS | p.G12D | 5 | 7 | 31% | 13% |
| KRAS | p.G12V | 9 | 21 | 63% | 10% |
| NRAS | p.Q61R | 12 | 16 | 37% | 9% |
| NRAS | p.Q61K | 12 | 16 | 37% | 8% |
| APC | p.R1450* | 7 | 10 | 28% | 8% |
| PIK3CA | p.E545K | 6 | 14 | 38% | 7% |
| TP53 | p.R175H | 6 | 6 | 17% | 7% |
| APC | p.R876* | 4 | 4 | 9% | 5% |
| KRAS | p.G13D | 1 | 1 | 1% | 4% |
| PIK3CA | p.E542K | 9 | 8 | 15% | 4% |
| FBXW7 | p.R465H | 17 | 26 | 59% | 4% |
| KRAS | p.A146T | 5 | 5 | 12% | 4% |
| EGFR | p.L858R | 10 | 11 | 34% | 3% |
| TP53 | p.R273H | 7 | 11 | 49% | 3% |
| APC | p.R216* | 11 | 18 | 46% | 3% |
| TP53 | p.R248W | 16 | 20 | 67% | 3% |
| IDH1 | p.R132C | 5 | 7 | 20% | 3% |
| TP53 | p.R213* | 9 | 28 | 67% | 3% |
| SMAD4 | p.R361H | 5 | 8 | 21% | 3% |
| APC | p.R1114* | 3 | 2 | 9% | 3% |

TABLE 3-continued

| GeneID | AA Mut | #Candidate Neoantigens | #HLA Class I Alleles with Predicted Binding | % North American Population Affected | Max Prevalence of Mutation in TCGA Major Cancer Types |
|---|---|---|---|---|---|
| KRAS | p.G12A | 8 | 18 | 62% | 3% |
| NRAS | p.Q61L | 11 | 17 | 50% | 3% |

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof

What is claimed is:

1. A method for prioritizing candidate neoantigens for a patient, the method comprising the steps of:
obtaining a plurality of candidate neoantigens;
determining self-similarity of members of said plurality;
determining similarity of members of said plurality to known antigens;
determining a level of expression of members of said plurality;
identifying a mutant allele frequency in exons encoding members of said plurality;
applying a rule to the results of the determining steps and identifying step to rank members of said plurality according to a likelihood of clinical significance; and
experimentally validating a subset of said plurality of candidate neoantigens based on the ranking.

2. The method of claim 1, further comprising preparing a report comprising the ranked members of the plurality of candidate neoantigens.

3. The method of claim 2, wherein one or more of the obtaining, determining, identifying, or applying steps are performed using a computer comprising a processor coupled to a tangible, non-transient memory and an input/output device.

4. The method of claim 3, further comprising sending the report to the output device.

5. The method of claim 1, wherein said plurality of candidate neoantigens is derived from a patient tumor sample.

6. The method of claim 1, wherein said plurality of candidate neoantigens is obtained by determining HLA genotype and MHC binding affinity for candidate peptides obtained from a tumor sample.

7. The method of claim 6, wherein the HLA genotype and the MHC binding affinity for candidate peptides is determined from in silico from peptide sequence data.

8. The method of claim 6, wherein the HLA genotype and the MHC binding affinity for candidate peptides are determined by assay.

9. The method of claim 6, wherein the candidate peptides are obtained by comparing peptides from the tumor sample to corresponding peptides from a normal sample, wherein candidate peptides comprise a mutation relative to the corresponding peptides.

10. The method of claim 6, wherein the applying step comprises removing candidate neoantigens having a MHC binding affinity of more than 1000 nM from the plurality of candidate neoantigens.

11. The method of claim 6, wherein the applying step comprises removing candidate neoantigens having a MHC binding affinity of more than 750 nM from the plurality of candidate neoantigens.

12. The method of claim 6, wherein the applying step comprises removing candidate neoantigens having a MHC binding affinity of more than 500 nM from the plurality of candidate neoantigens.

13. The method of claim 1, wherein the plurality of candidate neoantigens are each assigned an MHC classification of strong binding (SB) or weak binding (WB) and the applying step comprises ranking the plurality so that SB candidate neoantigens are ranked higher than WB candidate neoantigens.

14. The method of claim 1, further comprising:
determining antigen peptide processing classification of members of said plurality.

15. The method of claim 14, wherein the plurality is assigned a classification of epitope (E) or non-antigen (NA) and the applying step comprises ranking the plurality so that E candidate neoantigens are ranked higher than NA candidate neoantigens.

16. The method of claim 14, wherein the antigen peptide processing classification is determined using a peptide cleavage prediction or a transporter associated with antigen processing (TAP) affinity prediction.

17. The method of claim 1, wherein the applying step comprises ranking the plurality so that candidate neoantigens with lower self-similarity are ranked higher than neoantigens with higher self-similarity.

18. The method of claim 1, wherein the level of expression comprises an RNAseq expression value and the applying step comprises removing candidate neoantigens having an expression value below 10 reads per kilobase per million reads mapped (RPKM) from the plurality of candidate neoantigens.

19. The method of claim 1, wherein the applying step comprises removing candidate neoantigens having an expression value below 25 reads per kilobase per million reads mapped (RPKM) from the plurality of candidate neoantigens.

20. The method of claim 1, wherein the applying step comprises ranking the plurality based on 100 percent amino acid identity to portions of known antigens so that candidate neoantigens with amino acid identity to longer portions of known antigens are ranked higher than candidate neoantigens with amino acid identity to shorter portions of known antigens.

21. A method for identifying shared neoantigens, the method comprising the steps of:
selecting a plurality of recurrent mutations that occur in more than one tumor type;
determining, based upon predicted peptide sequence, which of said plurality are potential neoantigens;
determining self-similarity of members of said potential neoantigens;
determining similarity of members of said potential neoantigens to known antigens;
determining a level of expression of members of said potential neoantigens;
identifying said potential neoantigens as shared neoantigens based upon prevalence of HLA class I alleles and the prevalence of recurrent mutations across multiple tumor types; and
experimentally validating the shared neoantigens.

* * * * *